United States Patent [19]

Kimble et al.

[11] Patent Number: 4,994,598

[45] Date of Patent: Feb. 19, 1991

[54] OXIDATIVE CONVERSION OF ORGANIC COMPOUNDS

[75] Inventors: James B. Kimble, Bartlesville; John H. Kolts, Ochelata, both of Okla.

[73] Assignee: Phillips Petroleum Company, Bartlesville, Okla.

[21] Appl. No.: 484,033

[22] Filed: Feb. 22, 1990

Related U.S. Application Data

[60] Division of Ser. No. 180,873, Apr. 13, 1988, Pat. No. 4,925,997, which is a continuation-in-part of Ser. No. 947,235, Dec. 29, 1986, abandoned, Ser. No. 945,123, Dec. 22, 1986, Ser. No. 945,129, Dec. 22, 1986, and Ser. No. 938,907, Dec. 8, 1986, Pat. No. 4,774,216, which is a division of Ser. No. 742,340, Jun. 7, 1985, Pat. No. 4,658,077, and Ser. No. 938,895, Dec. 8, 1986, Pat. No. 4,775,654, which is a division of Ser. No. 713,673, Mar. 19, 1985, Pat. No. 4,658,076, and Ser. No. 891,009, Jul. 31, 1986, Pat. No. 4,895,823, which is a division of Ser. No. 713,674, Mar. 19, 1985, Pat. No. 4,672,145, Ser. No. 742,337, Jun. 7, 1985, and Ser. No. 742,335, Jun. 7, 1985.

[51] Int. Cl.$^5$ ............................................ C07C 255/08
[52] U.S. Cl. .................................................... 558/462
[58] Field of Search ............... 585/428, 426, 435, 440; 558/462

[56] References Cited

U.S. PATENT DOCUMENTS

| | | | |
|---|---|---|---|
| 2,614,130 | 10/1952 | Pines et al. | 585/428 |
| 3,494,956 | 2/1970 | Greene et al. | 260/465.8 |
| 3,557,235 | 1/1971 | Henry et al. | 260/668 |
| 3,960,923 | 6/1976 | DeSimone | 558/462 |
| 3,963,793 | 6/1976 | Weterings | 558/360 |
| 3,965,206 | 6/1976 | Montgomery et al. | 260/669 |
| 4,031,128 | 6/1977 | Khcheyan et al. | 558/462 |
| 4,254,293 | 3/1981 | Tremont et al. | 585/428 |
| 4,268,703 | 5/1981 | Williamson et al. | 585/428 |
| 4,268,704 | 5/1981 | Tremont et al. | 585/428 |
| 4,278,825 | 7/1981 | Tremont et al. | 585/428 |
| 4,278,826 | 7/1981 | Tremont et al. | 585/428 |
| 4,454,363 | 6/1984 | Teng et al. | 585/428 |
| 4,517,397 | 5/1985 | Terauchi et al. | 585/428 |
| 4,560,823 | 12/1985 | Gaffney | 585/658 |
| 4,620,057 | 10/1986 | Kimble et al. | 585/658 |
| 4,654,460 | 3/1987 | Kimble et al. | 585/658 |
| 4,658,076 | 4/1987 | Kolts et al. | 585/658 |
| 4,658,077 | 4/1987 | Kolts et al. | 585/658 |
| 4,672,145 | 6/1987 | Kolts et al. | 585/658 |
| 4,742,180 | 5/1988 | Gaffney | 585/658 |
| 4,774,216 | 9/1988 | Kolts et al. | 502/226 |
| 4,775,654 | 10/1988 | Kolts et al. | 502/226 |
| 4,925,997 | 5/1990 | Kimble et al. | 585/428 |

Primary Examiner—Asok Pal
Attorney, Agent, or Firm—K. K. Brandes

[57] ABSTRACT

A method for the oxidative conversion of feed organic compounds to product organic compounds, particularly, the conversion of toluene to bibenzyl and stilbene and the conversion of acetonitrile to acrylonitrile, in which the feed compounds are contacted with a free oxygen-containing gas and a contact material, comprising at least one Group IIA metal or lanthanum and oxygen; at least two Group IIA metals, Lanthanum Series metals, zinc, or titanium and oxygen; at least one Group IA metal, at least one Group IIA metal, Lanthanum Series metals, zinc or titanium and oxygen; at least one Group IA metal or Group IIA metal, phosphorous and oxygen; cobalt, at least one of zirconium, zinc, nickel, indium, lead or bismuth, phosphorous, at least one Group IA metal and oxygen; or cobalt, at least one Group IA metal, silicon and oxygen.

20 Claims, No Drawings

OXIDATIVE CONVERSION OF ORGANIC COMPOUNDS

The present application is a divisional application of U.S. patent application Ser. No. 180,873, filed Apr. 13, 1988 (now allowed) U.S. Pat. No. 4,925,997; which is a continuation-in-part of commonly owned U.S. patent application Ser. No. 947,235, filed Dec. 29, 1986, now abandoned; application Ser. No. 945,123, filed Dec. 22, 1986, application Ser. No. 945,129 filed Dec. 22, 1986; application Ser. No. 938,907, filed Dec. 8, 1986, now U.S. Pat. No. 4,774,216, which is a divisional application of application Ser. No. 742,340, filed June 7, 1985 (now U.S. Pat. No. 4,658,077); application Ser. No. 938,895, filed Dec. 8, 1986, now U.S. Pat. No. 4,775,654, which is a divisional application of application Ser. No. 713,673, filed Mar. 19, 1985 (now U.S. Pat. No. 4,658,076); application Ser. No. 891,009, filed July 31, 1986, now U.S. Pat. No. 4,895,823, which is a divisional application of application Ser. No. 713,674, filed Mar. 19, 1985 (now U.S. Pat. No. 4,672,145); application Ser. No. 742,337, filed June 7, 1985; and application Ser. No. 742,335, filed June 7, 1985.

BRIEF SUMMARY OF THE INVENTION

The present invention relates to the oxidative conversion of feed organic compounds to product organic compounds. In a more specific aspect, the present invention relates to the oxidative conversion of toluene to bibenzyl and stilbene isomers and the oxidative conversion of acetonitrile to acrylonitrile.

BACKGROUND OF THE INVENTION

Bibenzyl or diphenylethane is a valuable chemical intermediary. Likewise, isomers of stilbene are valuable chemical intermediaries, as well as having many other uses. More importantly, both bibenzyl and stilbene can be readily converted to styrene by known methods and styrene is a valuable monomer for the production of polymers. Numerous processes are known for the production of bibenzyl, such as treatment of benzyl chloride with metallic sodium, the action of benzyl chloride on benzyl magnesium chloride, etc. However, the most common method is the conversion of toluene to bibenzyl and stilbene isomers utilizing reducible metal oxide catalysts. Stilbene can also be produced by known methods, such as passing toluene over hot lead oxide. However, in all cases, the conversion and selectivity to bibenzyl and stilbene products is relatively low and improvement thereof is highly desirable.

Acrylonitrile is also a valuable chemical which is utilized in extremely large volumes for a wide variety of uses including the production of acrylic polymers. Processes for the production of acrylonitrile include the addition of hydrogen cyanide to acetylene with cuprous chloride, the catalytic conversion of acrylonitrile plus formaldehyde, the treatment of propylene, oxygen and ammonia with phosphomolybdate or a uranium-based compound, and the dehydration of cyanohydrin.

Another process for the production of acrylonitrile is the thermal or noncatalytic conversion of acetonitrile to acrylonitrile. This method of conversion, however, produces numerous unwanted products, particularly oxygenated products, which are difficult to remove from the desired products. In addition, conversion and selectivity are also comparatively low.

More recently, novel contact materials have been discovered which increase the conversion and selectivity to desired products in methods for the oxidative conversion of feed organic compounds to product organic compounds. While this discussion and the discussions hereinafter, at times, refer to certain components of these contact materials as "base materials" and others as "promoters", it is to be understood that these designations are made as a matter of convenience in identification, rather than by way of function. In all instances, the base materials, as well as the promoters, are active components of the contact material and the base materials are not inert "bases" or "carriers", as the designation sometimes indicates or implies.

Commonly assigned U.S. patent applications Ser. Nos. 713,653, 713,756 and 713,674, all filed on Mar. 19, 1985, relate to the use of Group IIA materials as base materials. Likewise, U.S. patent application Ser. No. 713,673, filed Mar. 19, 1985, relates to zinc as a base material. U.S. patent application Ser. No. 742,340, filed June 7, 1985, refers to titanium as a base material. U.S. patent application Ser. No. 742,337, filed June 7, 1985, refers to Lanthanum Series metals as base materials. U.S. patent application Ser. No. 945,129, filed Dec. 22, 1986 relates to certain combinations of these base materials. Each of these base materials is preferably promoted with a Group IA metal promoter. U.S. patent application Ser. No. 742,339, filed June 7, 1985 (now U.S. Pat. No. 4,620,057), relates to contact materials comprising cobalt, a metal selected from the group consisting of zirconium, zinc, nickel, indium, lead and bismuth, phosphorous, at least one Group IA metal and oxygen. Application Ser. No. 742,338, filed June 7, 1985, relates t ©the use of Group IA and/or Group IIA metal phosphates as contact materials. U.S. patent application Ser. No. 945,123, filed Dec. 22, 1986, relates to the use of a contact material comprising cobalt, at least one Group IA metal, silica and oxygen. All of the above-mentioned contact materials can also be further enhanced by the addition of a halogen thereto. In accordance with U.S. patent application 742,335, filed June 7, 1985, the halogen can be supplied by at least intervally adding the halogen or a halogen precursor to the reaction zone. U.S. application Ser. No. 947,235, filed Dec. 29, 1986, adds water to the feed in these techniques. The entire contents of each of these patent applications and patents are incorporated herein by reference.

SUMMARY OF THE INVENTION

It is therefore an object of the present invention to provide an improved method for the oxidative conversion of feed organic compounds to product organic compounds which overcomes the above and other disadvantages of the prior art. A further object of the present invention is to provide an improved method for the oxidative conversion of toluene to significant amounts of bibenzyl and stilbene in which the conversion and selectivity to the desired products is improved. A further object of the present invention is to provide an improved process for the oxidative conversion of acetonitrile to acrylonitrile wherein the conversion and selectivity to the desired products are improved. Yet another object of the present invention is to provide an improved method for the oxidative conversion of acetonitrile to acrylonitrile which does not produce oxygen-containing products. These and other objects of the present invention will be apparent from the following description.

The conversion of feed organic compounds to product organic compounds and the selectivity to product organic compounds are improved in accordance with the present invention which comprises:

a method for the oxidative conversion of a feed selected from the group consisting of toluene and acetonitrile, comprising:

contacting said feed and a free oxygen-containing gas with a contact material selected from the group consisting of:

(1) a solid contact material, comprising: (A) a metal selected from the group consisting of a Group IIA metal and lanthanum and (B) oxygen;

(2) a solid contact material, comprising: (A) at least two metals selected from the group consisting of Group IIA metals, Lanthanum Series metals, zinc and titanium and (B) oxygen;

(3) a solid contact material, comprising: (A) at least one metal selected from the group consisting of Group IA metals, (B) at least one metal selected from the group consisting of Group IIA metals, Lanthanum Series metals, zinc and titanium and (C) oxygen;

(4) a solid contact material, comprising: (A) at least one metal selected from the group consisting of Group IA metals and Group IIA metals, (B) phosphorous and (C) oxygen;

(5) a solid contact material, comprising: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, comprising: (A) cobalt, (B) at least one metal selected from the group consisting of Group IA metals, (C) silicon and (D) oxygen,

DESCRIPTION OF THE PREFERRED EMBODIMENTS

In its broadest aspect, the present invention comprises:

a method for the oxidative conversion of a feed selected from the group consisting of toluene and acetonitrile, comprising:

contacting said feed and a free oxygen-containing gas with a contact material selected from the group consisting of:

(1) a solid contact material, comprising: (A) a metal selected from the group consisting of a Group IIA metal and lanthanum and (B) oxygen;

(2) a solid contact material, comprising: (A) at least two metals selected from the group consisting of Group IIA metals, Lanthanum Series metals, zinc and titanium and (B) oxygen;

(3) a solid contact material, comprising: (A) at least one metal selected from the group consisting of Group IA metals, (B) at least one metal selected from the group consisting of Group IIA metals, Lanthanum Series metals, zinc and titanium and (C) oxygen;

(4) a solid contact material, comprising: (A) at least one metal selected from the group consisting of Group IA metals and Group IIA metals, (B) phosphorous and (C) oxygen;

(5) a solid contact material, comprising: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, comprising: (A) cobalt, (B) at least one metal selected from the group consisting of Group IA metals, (C) silicon and (D) oxygen, In a preferred embodiment, the contact materials are selected from the group consisting of:

(1) a solid contact material, consisting essentially of: (A) a metal selected from the group consisting of a Group IIA metal and lanthanum and (B) oxygen;

(2) a solid contact material, consisting essentially of: (A) at least two metals selected from the group consisting of Group IIA metals, Lanthanum Series metals, zinc and titanium and (B) oxygen;

(3) a solid contact material, consisting essentially of: (A) at least one metal selected from the group consisting of Group IA metals, (B) at least one metal selected from the group consisting of Group IIA metals, Lanthanum Series metals, zinc and titanium and (C) oxygen;

(4) a solid contact material, consisting essentially of: (A) at least one metal selected from the group consisting of Group IA metals and Group IIA metals, (B) phosphorous and (C) oxygen;

(5) a solid contact material, consisting essentially of: (A) cobalt, (B) at least one metal selected from the group consisting of zirconium, zinc, nickel, indium, lead and bismuth, (C) phosphorous, (D) at least one metal selected from the group consisting of Group IA metals and (E) oxygen; and (6) a solid contact material, consisting essentially of: (A) cobalt, (B) at least one metal selected from the group consisting of Group IA metals, (C) silicon and (D) oxygen.

Preferred Group IA metals utilized in the contact materials are selected from the group consisting of lithium, sodium and potassium.

Preferred Group IIA metals are selected from the group consisting of magnesium, calcium, strontium and barium.

Lanthanum Series metals are preferably selected from the group consisting of lanthanum, praseodymium, samarium and terbium. Lanthanum is preferred.

Contact material (5) preferably includes zirconium. When a Group IA metal is utilized in this contact material, it is preferably selected from the group consisting of lithium, sodium and potassium, preferably sodium, and still more preferably, both sodium and potassium.

Contact material (6) preferably contains lithium, as a Group IA metal, and still more preferably, a combination of lithium and sodium.

All of the subject contact materials may also contain halogen ions, or compounds containing halogen ions, as a component, preferably chlorine.

Contact materials (1), (2), (3) and (6) may also contain phosphorous, or compounds containing phosphorous, as a component and contact material (6) preferably contains both phosphorous and a halogen.

Contact materials (5) and (6) may also optionally contain sulfur or a compound containing sulfur.

While the exact compositions and nature of the contact materials are not known, it is believed that, irrespective of the starting materials, the components are converted to their oxide form during calcination. Accordingly, with the exception of phosphorous, it is believed that all components are present as oxides or mixed oxides. It is believed that phosphorous is present as a phosphate or pyrophosphate. Where a halogen is present it is believed that the halogen is present as a halide. Where sulfur is present, it is believed that it is present as a sulfate. By the same token, it is not known what changes the contact materials go through during the course of a reaction, and it is possible that oxides may be converted to carbonates, and that like changes may take place with reactants, products or by-products.

The contents and relative proportions of the various components of the contact materials do not appear to be highly critical in most cases. Accordingly, when the term "effective amount" is utilized, with reference to the content of the components of the contact materials herein, this term is meant to include more than an insignificant amount and, thus, a small amount sufficient to effect the function of the contact material for the purpose for which it is utilized. Accordingly, any of the components of the contact materials may be present in amounts anywhere from an effective amount to near 100 percent, for example, between about 0.05 and 99.95 weight percent, expressed in terms of the elemental metal based on the total weight of the contact material. This is particularly true of the materials referred to herein as "base" materials in contact materials (1), (2) and (3), and the cobalt of contact material (6). Most importantly, such amounts or proportions apply when the contact material contains two or more of the base materials in combination, since a small amount of one base material can be utilized and is effective in improving the contact material when mixed with an extremely large amount of a second base material. However, preferred contact materials do contain certain compounds in major proportions, and other compounds in minor proportions, and it is for this reason that certain compounds are referred to as "base" materials, while others are referred to as "promoters".

Where Group IA and/or Group IIA metals are utilized in contact materials (1), (2), (3), (4) or (5) and they are not in the form of electrically balanced compounds with the base or major component, such Group IA and Group IIA metals are preferably utilized in minor amounts, usually between about 0.1 and 50 weight percent, still more preferably, between about 0.5 and 15 weight percent, and optimally, between about 1 weight percent and about 5 weight percent, expressed in terms of the elemental metal based on the total weight of the contact material. Halogens are also preferably utilized in minor amounts, usually between about 0.1 weight percent and 5 weight percent, expressed as elemental halogen based on the total weight of the contact material. In contact material (5), the cobalt and the metal selected from the group consisting of zirconium, zinc, niobium, indium, lead and bismuth are utilized as major components, while the remaining components are utilized in minor amounts. By way of example, the preferable atomic ratio of cobalt to the metals selected from the group consisting of zirconium, zinc, niobium, indium, lead and bismuth is in the range of about 1/1 to about 20/1 and more preferably, in the range of about 3/1 to 6/1.

The phosphorous in all contact materials is preferably present in an amount of about 1 weight percent to about 10 weight percent and more preferably, between about 2 weight percent and about 5 weight percent, expressed in terms of phosphorous oxide based on the total weight of the contact material. Preferably, the alkali metal of contact material (5) is present in concentrations of about 1 weight percent to about 10 weight percent and more preferably, between about 2 weight percent and about 5 weight percent, also expressed in terms of alkali metal oxide based on the total weight of the contact material. Preferred concentrations of sulfur are in the range of about 1 weight percent to about 10 weight percent and, more preferably, between about 2 weight percent and about 5 weight percent, expressed in terms of elemental sulfur based on the total weight of the contact material. The halogen in contact material (5) is preferably present in an amount between about 1 weight percent and about 10 weight percent and, more preferably, between about 2 weight percent and about 5 weight percent, expressed in terms of elemental halogen based on the total weight of the contact material.

In contact material (6), the amounts of some of the components do appear to be somewhat critical. As previously indicated, the amount of cobalt may range from an effective amount to near 100 percent. However, due to the expense and difficulty of obtaining cobalt, it is preferred that the cobalt be present in amounts between about 0.05 and 50 weight percent, preferably, 0.05 to 20 weight percent, and, still more preferably, between about 0.05 and 10 weight percent, again expressed in terms of elemental cobalt based on the total weight of the catalyst. The same principles apply to the content of alkali metals, phosphorous, halogen and sulfur, as applied to the previously discussed contact materials. However, the alkali metals other than sodium are preferably present in amounts between about 0.01 and 30 weight percent, and, still more preferably, between about 0.05 and 15 weight percent, expressed in terms of elemental alkali metal based on the total weight of the catalyst. Sodium may also be utilized in these amounts but, preferably, when utilized in combination with another alkali metal, particularly lithium, the sodium should be present in amounts between about 0.05 and 1.0 weight percent and more preferably, between about 0.05 and 0.8 weight percent. The balance of this contact material is, of course, silicon in the form of silica. In any event, the base materials of contact materials (1), (2) and (3), the combination of cobalt and zirconium, zinc, nickel, indium, lead or bismuth of contact material (5), and the silica of contact material (6) are all preferably present in amounts of at least 50 weight percent, with the total content of the other components or promoters, being less than about 50 percent.

The above-mentioned components can be mixed with or deposited on an "inert support material" adapted to harden or support the active materials. The term "inert support material" when utilized in this context, is meant to include any material which does not react with or exchange ions with the active components, has no significant functional effect on the production of desired or undesired products in the process for which the solid contact material is utilized, and functions only as a hardening agent or support for the active components. Where such solid support material is utilized, the weight of such solid support material is not included in the relative weights of the active components set forth above.

The components of the contact material can be derived from any suitable source of such materials, such as carbonates, oxides, hydroxides, nitrates, octoates, chlorides, phosphates, sulfides and sulfonates, of an organic or inorganic nature. The contact materials can be prepared by any suitable method, known in the art, for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations.

In general, any method can be used which provides compositions of matter containing the prescribed components in effective amounts. When slurries, precipitates or the like are prepared, they will generally be dried, usually at a temperature sufficient to volatilize the water or other carrier, such as about 220° F. to about 450° F. In all cases, irrespective of how the components are combined and irrespective of the source of the components, the dried composition is calcined in the presence of a free oxygen-containing gas, usually at temperatures between about 600° F. and about 1500° F. for from 1 to about 24 hours. As pointed out hereinafter, contact material (5) can be calcined in a reducing or inert atmosphere or an oxygen-containing atmosphere.

The manner in which the contact materials of the present invention perform the reaction-promoting function is not fully understood. Accordingly, the present invention is not to be limited to any particular theory. However, several significant observations have been made in parallel work and in accordance with the present invention.

First, each of the components of contact materials (1), (2), (3), (4), (5) and (6), unless designated as optional, appear necessary and participate in the reaction promoting function thereof. Hence, simply because a particular component is present in an minor amount it cannot be categorized as a "promoter" or "active" component and the components present in major proportions cannot be categorized as inert "bases", "carriers" or "supports".

Secondly, the contact materials do not promote oxidative conversion reactions when utilized in the absence of a free oxygen-containing gas; or, such use results in insignificant conversion of feed organic materials and/or insignificant selectivity to product organic compounds.

Finally, it has been observed, in accordance with the present invention, that contact material (5) results in very poor conversion and/or selectivity, if it is in a high state of oxidation, and reduction of the state of oxidation is highly desirable.

Based on these observations, it can be concluded that, irrespective of whether multivalent components are present in the contact materials, the reaction mechanism of the present invention is not oxidation-reduction. Accordingly, at least when the reactions are carried out in the presence of a free oxygen-containing gas, in accordance with the present invention, it is not necessary that the contact material include multivalent components capable of undergoing oxidation-reduction or redox reactions, as taught by many workers in prior art.

It has also been found, in accordance with the present invention, that the halogen of the contact materials becomes depleted during the course of oxidative conversion in the presence of a free oxygen-containing gas. Accordingly, when carrying out the oxidative conversion reaction, in accordance with the present invention, a material containing at least one halogen, or halogen precursor, such as gaseous halogen, for example, chlorine, methylchloride, methylenechloride and like compounds of the other halogens, is at least intervally contacted with the contact material. The material containing the halogen is preferably a normally gaseous material or will be in a vapor state under the operating conditions of the oxidative conversion reaction. In any event, in accordance with the present invention, the reaction-promoting activity of the contact material can be maintained throughout the conduct of the method by continuously adding the material containing the halogen to the organic feed compounds and free oxygen-containing gas, or by adding the material containing the halogen at intervals during the conduct of the method. In the latter case, the flow of feed organic compounds and free oxygen-containing gas can be discontinued during the addition of the material containing the halogen, although this is not necessary.

The state of oxidation of solid contact materials (1), (2), (3), (4) and (6) does not appear to be critical and, normally, it is not necessary to contact any of these contact materials with a reducing agent in order to maintain their reaction-promoting activity. However, when these contact materials have been utilized in long production runs, occasional contacting of the contact material with a reducing agent may be beneficial. On the other hand, as indicated previously, the reaction-promoting effect of solid contact material (5) does appear to be affected by the degree of oxidation thereof. It has been found that, after a period of use, in the presence of a free oxygen-containing gas, there is a tendency for this contact material to become "overoxidized" and lose its reaction-promoting activity. However, in accordance with the present invention, it has been found that the reaction-promoting activity of this contact material can be maintained at near its peak activity by intervally contacting the solid contact material with a material containing at least one reducing agent.

It has also been discovered that the solid contact materials of the present invention can be prepared without, or with only small amounts of the halogen component, and such component can be added by, thereafter, treating the calcined contact material with a material containing at least one halogen, or halogen precursor, preferably in a gaseous or vapor state. Such treatment can be preformed prior to disposing the contact material in the reaction zone in which the oxidative conversion reaction is to be carried out, but, preferably the calcined contact material is disposed in the reaction zone and treated with the halogen prior to the introduction of the organic feed material and free oxygen-containing gas, or along with the first portion of the organic feed and oxygen. This technique also results in more active contact materials, since it has also been found that, in at least some cases, it is difficult to incorporate an effective amount of halogen in the contact material during preparation and/or retain an effective amount of halogen in the contact material during preparation, particularly during calcining.

Contact material (5), as previously indicated, has another peculiarity, namely, that it produces substantially superior results if it is in a lower state of oxidation. Normally, in the preparation of this contact material, the combined components are dried in the presence of a free oxygen-containing gas, usually air. As a result of the presence of the air at an elevated temperature, it is believed that at least some of the components of the contact material are in a high state of oxidation after drying and, therefore, are inefficient contact materials for the oxidative conversion reaction. Consequently, it has been the past practice to calcine the dried contact material in an inert or reducing atmosphere in order to reduce the oxidation level of the material. This, of course, is difficult and adds to the expense of preparation. In accordance with the present invention, it has been found that the combined air-dried components of the contact material may be calcined in a conventional manner in the presence of a free oxygen-containing gas, usually air, and, thereafter, pretreated, to reduce the level of oxidation, by contacting the calcined contact material with a material, including at least one reducing material. Suitable reducing materials include hydrogen and lower alkanes such as methane, ethane, etc. Contact material (5) can also be prepared without halogen, or with only a small amount of halogen, and the halogen also added during the pretreatment. Consequently, the pretreatment comprises contacting the air calcined contact material with both a material containing at least one halogen and a material containing a reducing agent. Such contacting may be simultaneous or in either sequence.

The free oxygen-containing gas may be any suitable oxygen-containing gas, such as oxygen, oxygen-enriched air or air. The method of the present application has been effectively carried out utilizing air as a source of oxygen.

The volumetric ratio of organic compound to free oxygen, expressed in terms of gaseous or vapor phase, should be in excess of about 1/1, preferably it is between about 1/1 and about 30/1, and still more preferably, between about 4/1 and about 15/1. It has been found that a ratio of organic compound to free oxygen of at least about 1/1 is necessary, in accordance with the present invention, in order to obtain maximum conversion of organic compound and high selectivity to desired products. The volumetric ratio of water to $CH_4$ is between about 0.25/1 and 30/1 and preferably, between 0.25/1 and 10/1, also expressed in terms of the gaseous or vapor phase.

The method of the present invention may be carried out over a wide variety of conditions.

The temperature is preferably at least about 500° C. and will generally vary between 500° C. and about 1500° C. For the conversion of toluene, it is preferably between about 500° C. and 700° C. For the conversion of acetonitrile, it is preferably between about 600° C. and 800° C. The total pressure may vary anywhere from around 1 atmosphere to about 1500 psi but are preferably, below about 300 psi and ideally, below about 100 psi.

The total flow velocities of all gaseous or vaporous materials and including diluents, through a fixed bed reactor, may be at any rate effective for the oxidative conversion reaction. For example, from 50 to 10,000 GHSV and preferably between about 500 and 5,000 GHSV.

The following examples illustrate the operation of the present invention and its advantages.

EXAMPLE I

Since lithium on magnesium, both in their oxide form, is representative of the catalysts of the present invention, the present example was carried out utilizing a catalyst comprising 3 weight percent of lithium on magnesium oxide, expressed in terms of elemental lithium based on the total weight of the catalyst. The reaction was carried out utilizing a toluene to oxygen ratio of 5/1 at the temperatures indicated. The feed ratio of toluene/oxygen/nitrogen was 5.7/1/4. The condensed phase products and the selectivities, based on apparent toluene conversion, are set forth in Table I below.

TABLE I

| Run # | cc/min. | | | GHSV | Temp. | Conv. | Selectivity | | |
|---|---|---|---|---|---|---|---|---|---|
| | $N_2$ | $O_2$ | Tol. | | | | Benzene | Bibenzyl | Stilbene |
| 1 | 60 | 15 | 75 | 360 | 625 | 2 | 22 | 68 | 10 |
| 2 | 60 | 15 | 75 | 360 | 600 | 2 | 22 | 72 | 6 |
| 3 | 60 | 15 | 75 | 360 | 575 | 1 | | 100 | |
| 4 | 60 | 15 | 75 | 360 | 590 | .4 | 5 | 95 | — |

It is to be observed from the above results that both significant improvement in the conversion of toluene and the selectivity to bibenzyl and stilbene is obtained, particularly at the higher temperatures, as compared with control run #4 which utilized no catalyst.

EXAMPLE II

In a second set of runs, acetonitrile (ACON) was oxidatively converted in run #1 utilizing quartz chips (inert material) and a gas feed rate of 360 cc/min. methane and 40 cc/min. of oxygen. In the second run, a catalyst comprising 3 weight percent of lithium deposited on calcium titanate, expressed in terms of elemental lithium based upon the total weight of the catalyst, utilized 360 cc/min. of nitrogen and 40 cc/min of oxygen. The following Table sets forth the results of this test showing the conversion of acetonitrile and selectivity to carbon oxides, acrylonitrile (ACRON) and proprionitrile (PPON).

TABLE II

| Run No. | °C. Temp. | cc/hr. ACON | % Conv. | Selectivity (%) | | |
|---|---|---|---|---|---|---|
| | | | | $CO_x$ | ACRON | PPON |
| 1 | 600 | 8.64 | 3 | 69 | 5 | 9 |
| 2 | 600 | 8.64 | 19 | 71 | 23 | 1 |

It is to be seen from the previous Table that the catalyst produces a much higher conversion than the thermal process at a given temperature. It is also to be noted that considerably more of the $C_3$ product is acrylonitrile rather than propionitrile. This, too, is in contrast to the thermal method. Finally, while not shown, a substantial decrease in $C_4$ products is obtained with the catalyst, as opposed to the noncatalytic process.

While specific materials, conditions of operation, modes of operation and equipment have been referred to herein, it is to be recognized that these and other specific recitals are for illustrative purposes and to set forth the best mode only and are not to be considered limiting.

That which is claimed:

1. A method for the oxidative conversion of feed organic compounds comprising acetonitrile, comprising:
    contacting said feed organic compounds and a free oxygen-containing gas with a solid contact material comprising (A) lanthanum, or, alternatively, at least two metals selected from the group consisting of Group IIA metals, Lanthanum Series metals, zinc and titanium, and (B) oxygen;
    under reaction conditions wherein said acetonitrile is converted to acrylonitrile.

2. A method in accordance with claim 1, wherein component (A) of said solid contact material is lanthanum.

3. A method in accordance with claim 2, wherein said solid contact material additional comprises halogen ions.

4. A method in accordance with claim 2, wherein said solid contact material additionally comprises phosphorous.

5. A method in accordance with claim 1, wherein said solid contact material comprises (A) at least two metals selected from the group consisting of Group IIA metals, Lanthanum Series metals, zinc and titanium, and (B) oxygen.

6. A method in accordance with claim 5, wherein said Group IIA metals are magnesium, calcium, strontium and barium, and said Lanthanum Series metals are lanthanum, praseodynium, samarium and terbium.

7. A method in accordance with claim 5, wherein said solid contact material additionally comprises halogen ions.

8. A method in accordance with claim 5, wherein said solid contact material additionally comprises phosphorous.

9. A method in accordance with claim 5, wherein said solid contact material comprises calcium titanate.

10. A method in accordance with claim 5, wherein one of said at least two metals in said solid contact material is titanium.

11. A method in accordance with claim 5, wherein said solid contact material comprises a Group IIA metal and titanium.

12. A process in accordance with claim 1, wherein said contacting is carried out in the presence of added water.

13. A method in accordance with claim 1, wherein said contacting is carried out in the presence of an added halogen precursor.

14. A method in accordance with claim 1, wherein said contacting is carried out at a volumetric ratio, in the vapor phase, of said feed organic compounds to said free oxygen of about 1/1 to about 30/1, and a temperature of about 500° C. to about 1500° C.

15. A method in accordance with claim 5, wherein one of said at least two metals in said solid contact material is zinc.

16. A method in accordance with claim 5, wherein said solid contact material comprises zinc and titanium.

17. A method in accordance with claim 5, wherein one of said at least two metals in said solid contact material is a Lanthanum Series metal.

18. A method in accordance with claim 17, wherein said Lanthanum Series metal is lanthanum.

19. A process in accordance with claim 5, wherein said solid contact material comprises a Lanthanum Series metal and titanium.

20. A process in accordance with claim 19, wherein said Lanthanum Series metal is lanthanum.

* * * * *